United States Patent [19]

Abel et al.

[11] 4,254,338

[45] Mar. 3, 1981

[54] DETERMINATION OF TEMPERATURE DISTRIBUTIONS ON AWKWARDLY LOCATED OR LOW-ACCESS SURFACES

[75] Inventors: Otto Abel, Clausthal-Zellerfeld; Hans-Josef Giertz, Ratingen; Joachim Hoppe, Mülheim, Saan; Werner Eisenhut, Essen; Bhubaneswar Sarangi, Recklinghausen; Günter Serwatzky, Bonn-Bad Godesberg, all of Fed. Rep. of Germany

[73] Assignee: Bergwerksverband GmbH, Essen, Fed. Rep. of Germany

[21] Appl. No.: 915,066

[22] Filed: Jun. 12, 1978

[30] Foreign Application Priority Data

Apr. 18, 1978 [DE] Fed. Rep. of Germany ....... 2816725

[51] Int. Cl.³ .................... G01J 1/00; G01F 23/00; C21D 11/00
[52] U.S. Cl. .................... 250/340; 250/357; 266/87
[58] Field of Search .............. 250/338, 340, 342, 357; 266/80, 87

[56] References Cited

U.S. PATENT DOCUMENTS

3,588,067 6/1971 Shimotsuma et al. ............... 266/80
4,110,617 8/1978 Legille ........................... 250/342

Primary Examiner—Alfred E. Smith
Assistant Examiner—Janice A. Howell
Attorney, Agent, or Firm—Michael J. Striker

[57] ABSTRACT

An infrared heat-image camera is aimed at a hot surface not perpendicular thereto but instead in a direction almost parallel to the surface, presenting to the camera a heat image of the surface not cartesian but instead highly distorted in accordance with the laws of optical perspective. The camera's output data is correspondingly non-cartesian and distorted with respect to organization and content, but the data is applied to a computer which transforms it to cartesian organization and corrects content, and then a corrected cartesian display is generated, simulating the heat image which would be presented to a perpendicularly aimed camera. Alternatively, the camera's scanning mechanisms are programmed to follow a non-cartesian scanning schedule, the geometry of which itself causes the camera output data to have the cartesian organization of a perpendicularly aimed camera. Preferably, the scanning schedule is modified to effect transformation to cartesian organization in only one direction, and transformation to cartesian organization in the other direction is computer-performed.

12 Claims, 10 Drawing Figures

DETERMINATION OF TEMPERATURE DISTRIBUTIONS ON AWKWARDLY LOCATED OR LOW-ACCESS SURFACES

BACKGROUND OF THE INVENTION

The present invention relates to methods and apparatuses for determining the temperature distribution over a surface, using means of the type which do not require physical contact with the surface, and particularly in cases where problems of spatial access do not permit the temperature sensing means to be aimed perpendicular to the surface of interest.

In many fields of technology, it is desired to ascertain the temperature distribution across a surface, to be able to detect the presence and location of hot-spots or other locations where the prevailing temperature deviates from a desired temperature profile. However, as a practical matter, such surfaces may be so located, e.g., behind interfering structures, as to make direct and simple access to such surfaces impossible. For example, it may be desired to ascertain the temperature profile of a very large surface from within a very confined space.

A representative example of this sort of problem is found in coking technology. Each coking chamber in a battery of coking ovens is typically rectangular, has a vertical height on the order of up to 8 meters, a horizontal length on the order to up to 17 meters, but a width on the order of only about 0.4 to 0.5 meters. Accordingly, the interior space of one such coking oven is quite tall, deep and narrow. The temperature profile of, for example, the interior side walls of the coking chamber is of great technological importance, because of the information it yields concerning the uniformity of the coking operation which will occur within the chamber and thereby the quality of the coke to be produced. However, attempts to scan the temperature of the interior side wall of the coking chamber are made very difficult by problems of access. The interior side walls can only be viewed through one of the doors at the two ends of the coking chamber or through a charging opening at the top of the chamber. The direction of view towards the side wall, when looking into the chamber through an end door or charging opening, is of course not at all perpendicular to the surface of the side wall, and indeed will be nearly parallel to the sidewall.

It is well known to ascertain the temperature profile across a surface of interest using so-called infrared T.V. cameras operative for producing heat images. However, when infrared T.V. cameras are employed, it is necessary that the optical axis of the camera be oriented generally perpendicular to the surface of interest, and of course at a great enough distance from the surface of interest when the latter is very large. This is necessary, in order that the field of view of the infrared temperature-detecting camera actually capture the surface of interest, and also in order that the surface elements scanned by the infrared camera present themselves to the camera substantially equally to avoid heat-image distortion. Such equipment is not employed where spatial problems prevent such a set-up. For example, in a coking chamber, the temperature in the interior of the chamber is extremely high, the surface area of the interior side walls very large, and the distance from which the camera could be perpendicularly spaced from the side wall extremely small, making the use of such a technique impossible.

Therefore, in applications such as this, considerable work has been done to develop alternative techniques for ascertaining temperature profiles. Thus, it is known to measure the temperatures of the interior side walls of coking chambers using optical pyrometers inserted through the charging openings at the tops of the coking chambers. However, such pyrometers are basically capable of measuring the temperature of only individual surface points, and therefore cannot readily generate information indicating the temperature profile across the whole, and rather large surface of the side wall; attempts to use such pyrometers to generate a whole temperature profile across the whole side-wall surface are so time-consuming as to be impractical for routine use during routine operation of the coking-oven battery.

Published allowed German Federal Republic patent application DT-AS No. 12 25 143 discloses a method for measuring the temperatures of wall surfaces. This technique involves the use of a radiation detector mounted on a rod. The rod is displaced to cause the radiation detector to travel along and parallel to the wall surface of interest. However, this system is very problematic. If only a single radiation detector is employed, what is ascertained is merely the temperature profile along a narrow line of the large wall surface. Even if one employs a plurality of such detectors spaced perpendicular to the scanning direction, this merely generates such information for a plurality of narrow lines of the large wall surface. Despite the expense, information establishing a temperature profile across the whole surface area of the wall, cannot be practically generated. Also, this type of system is burdened by a great deal of generated misinformation, resulting from temperature differences as between the wall surface and the measuring equipment itself.

SUMMARY OF THE INVENTION

It is the general object of the present invention to be able to generate data representing the temperature profile across the entire surface of interest, although the measuring equipment employed be aimed at the surface at angles anywhere from 90° (as is conventional) down to as low as nearly 0°, the generated data being of rectangular organization and undistorted (i.e., accurate) despite even the use of very non-perpendicular angles of aim.

This object can be achieved, in accordance with the most general concept of the invention, by using a two-dimension temperature scanning system, of a type which need not physically contact the surface of the interest. Of course, a two-dimension temperature scanning system (such as the conventional infrared T.V. cameras mentioned above) is basically capable of generating a true surface temperature profile, i.e., information concerning every point of the whole surface of interest. However, when the two-dimension temperature scanning system is aimed at the surface of interest at an angle of aim which is far from perpendicular to the surface, and indeed in some cases almost parallel to the surface, there arise problems of distortion in both the generated temperature data per se and also in the organization of the temperature data. The present invention proposes to scan the surface of interest in a series of adjoining strips, and to eliminate the distortion in the generated temperature data and in the organization of the data by (a) using an electronic computer to transform the organization of the generated temperature data into a rectangular (cartesian) organization of accurate temperature data, or (b) during the scanning operation, continually varying the horizontal and/or vertical deflection schedules of the scanning system in accordance with a preestablished program which takes into account the non-perpendicular angle of aim, or (c) using a combination of techniques (a) and (b).

This will be explained in greater detail below.

The present invention makes it possible, even in situations of highly problematic spatial access to the surface of interest, to generate a true 2-dimensional display, tabulation or record of a true surface-area temperature profile, the organization of the data being cartesian (i.e., corresponding to the actual surface of interest), and the data being, of course, accurate.

With the present invention, it becomes possible for example to be able to automatically regulate the feed of heating gas to a coking chamber such that surface zones which deviate from the designed temperature profile for the chamber interior are accurately brought to correct temperature, which improves the quality of the coke produced and also the economy of operating the coking installation in general. Additionally, the amount of time required to perform the temperature scanning, and the personnel costs involved in it, represent a fraction of what is typical for comparable prior-art attempts. In the context of a battery of coking chambers, a single scanning system can be moved along the battery from one chamber to the next, representing a very great economy compared to those prior-art techniques in which each chamber is provided with temperature-sensing means of its own.

The temperature-scanning system presently preferred is a passive infrared system.

In the preferred embodiment of the invention, the scanning of the surface of interest is performed on a stripwise or linewise basis. The temperature scanning system scans along successive scanning strips, and the measuring equipment is displaced, in the direction perpendicular to the strip-scanning direction, at a preprogrammed velocity which takes into account the non-perpendicular angle of aim of the system. In this way, the density of or packing of the successive scanned strips is equalized, i.e., so that as the scanning system proceeds to stripwise scan parts of the surface which are first near and then far from the scanning system, strip-shaped zones of the scanned surface are not skipped during the scanning process, nor do scanned strips overlap; i.e., the whole surface of interest is scanned uniformly. If the preprogrammed velocity just referred to is so selected as to permit the skipping or overlapping of strip-shaped zones of the scanned surface, or otherwise non-uniform scanning the distortion entering into the resulting temperature data and its organization is likewise eliminated by an electronic computer.

Figures 1A, 1B:
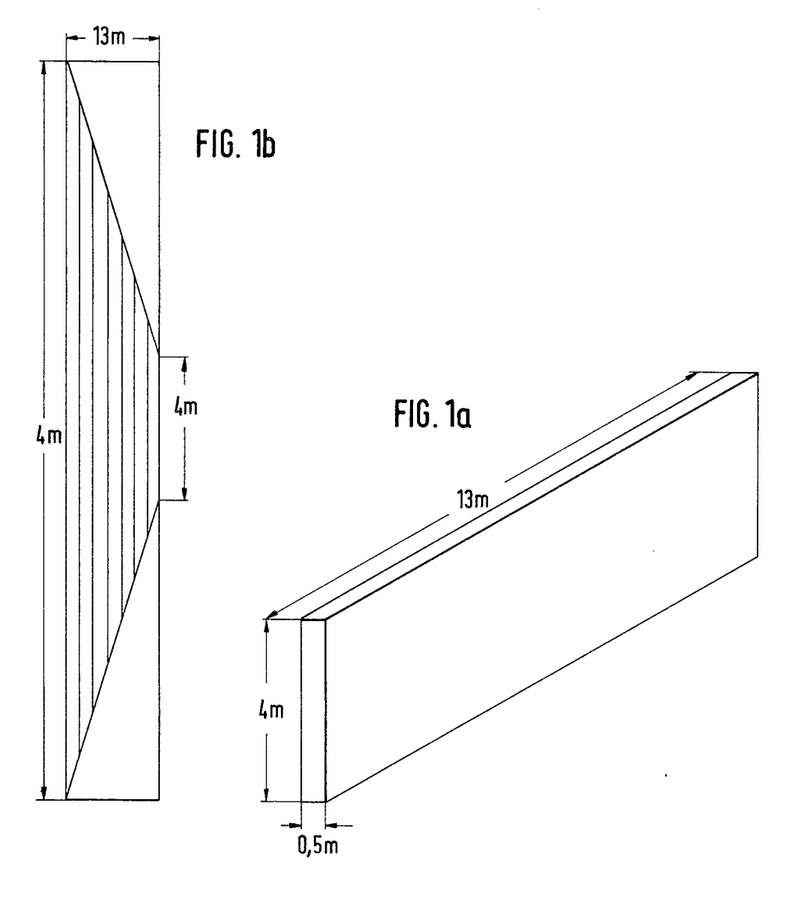
FIG. 1a depicts the typical dimension of a coking chamber.
FIG. 1b depicts the appearance of the left interior side wall of such a coking chamber, to a viewer or viewing system peering into an open end door of the chamber.
Figure 2:
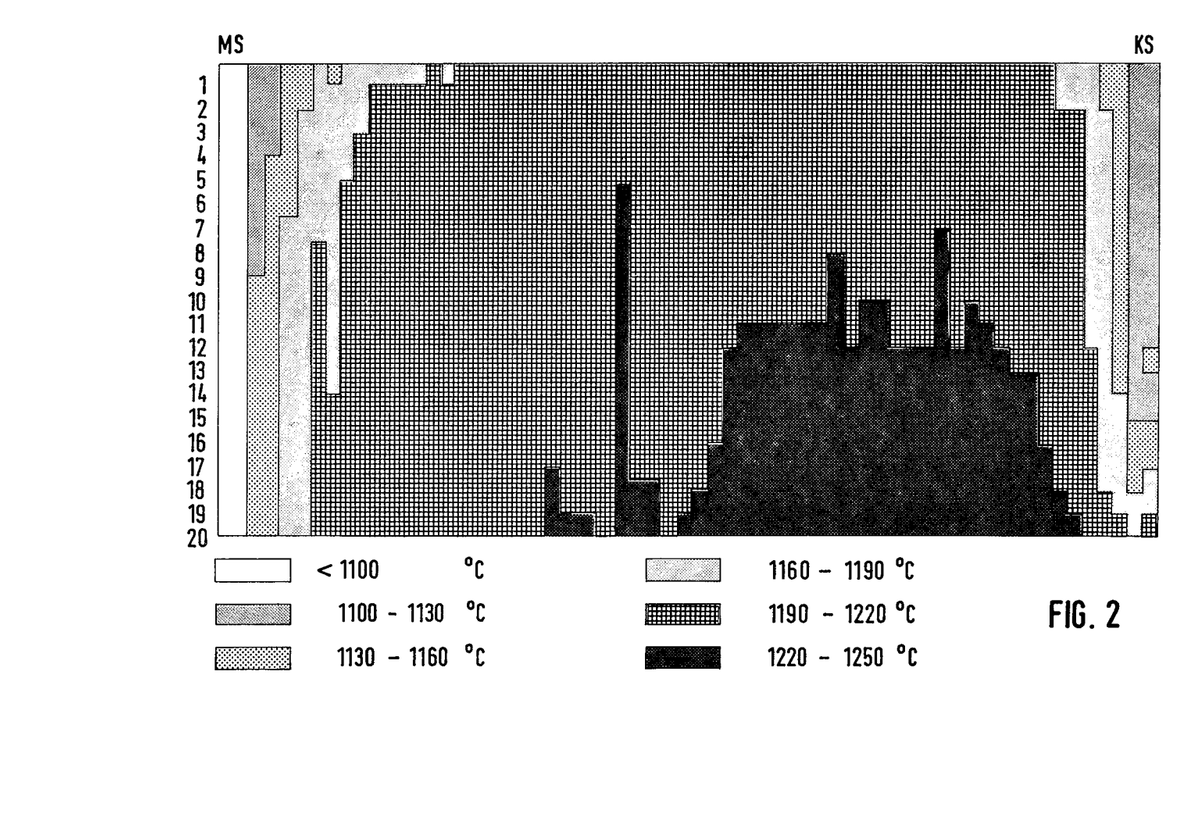
FIG. 2 depicts the character of the cartesian tabulation, print-out or display of the two-dimensional temperature profile of the surface of interest.

Reference is made to FIGS. 1a, 1b and 2, to make clear the type of problem to be faced and the type of data to be generated. FIG. 1a depicts typical dimensions of a coking chamber in a battery of such chambers, i.e., 4 meters tall, 13 meters deep and only 0.5 meters wide. Such chambers are provided, at each of their two 0.5×4 m ends with end doors, and at their 0.5×13 m tops with charging openings. FIG. 1b depicts the view into the interior of such a coking chamber, and particular the view of its left interior side wall, as seen by a human observer, or by an infrared heat-image camera, peering in through an open end door. The direction of aim of the infrared heatimage camera, or of the eyes of a human observer, here makes an angle of about 88° relative to the normal to the left side wall; i.e., the part of the left side wall farthest from the viewer or viewing system is viewed at an angle of only about 2° relative to the wall surface itself. The field angle (hereinafter referred to as the angle of view) for the viewer is about 125° when viewing the part of the surface nearest the viewer and about 16° when viewing the part of the surface most remote from the viewer.

Located outside the coking chamber, at the open end door of the coking chamber, is a passive infrared temperature scanning system mounted on a carriage. The carriage is so designed that the scanning system can be swung and/or shifted in the horizontal direction, to scan left-right. The scanning system is mounted halfway between the top and the bottom of the coking chamber. The speed at which the scanning system is swung and/or shifted on its carriage is variable, and is varied in accordance with a preestablished program. The optical axis of the scanning system is oriented generally parallel to a diagonal of the floor of the coking chamber. The internal mechanism of the scanner causes the scanner's radiation detector to receive in succession radiation from successive surface elements located along a scanned line or strip of the wall surface. This is repeated for successive scanned strips. After each stripscan, the scanner is horizontally swung or shifted on its carriage a preprogrammed amount, and in this way the whole surface of interest is scanned. Considering only the scanning of a single strip, i.e., a single strip-scan, the vertical angle of view of the scanner is constant at about 120°, and the horizontal angle of view of the scanning is constant at about 0.075°. The horizontal angle of view (field angle) is extremely narrow and precise, for a single strip-scan.

The output data from the scanner is recorded on magnetic tape, then fed into an electronic computer which reorganizes and corrects it, to take into account the highly non-perpendicular direction of aim of the scanner, i.e., to take into account the distortion in the shape and size of the surface element scanned at any given instant. After this temperature data has been thusly reorganized and corrected, the output data from the computer is applied to a tabulator, display and/or T.V. screen, upon which appears a print-out or display such as shown in FIG. 2.

Alternatively, it is possible to control the horizontal and vertical angles of view of the scanner, i.e., to vary them during the course of the scanning of the wall surface in accordance with a preestablished program, to take account, already at that stage, the distortion resulting from the direction of aim, so that the output data from the scanner when recorded e.g., on magnetic tape is already at that point in proper cartesian organization.

Finally, it is likewise possible to vary the angle of view of the scanner in only one direction during the scanning, again in accordance with such preestablished program, and then use the computer to finish the transformation into cartesian organization.

Actually, the present invention can of course be practiced using a variety of different measuring techniques.

Preferably, the scanning system is mounted on a subframe which is transportable or even vehicular, can be arrested definitely in a selected position, and is provided with means for performing coarse-adjustment levelling of the subframe. In this way, the subframe mounting the scanning system can be moved from one measuring location to the next, e.g., from one coking chamber to the next in a battery of such chambers. By whatever means the subframe is transportable, it must be very precisely and definitely arrestable in a selected position, so that the position and orientation of the scanning system relative to the wall surface of interest can be absolutely maintained during the course of a scanning operation and also during the course of preliminary set-up work.

Providing the subframe with means for performing coarse-adjustment levelling of the subframe at three or four points, e.g., at its corners, in conjunction with fine-adjustment levelling means for the scanning system, greatly facilitates establishing the proper position and orientation for the scanning system. It has been found that the resolution and accuracy of the inventive technique is greatly dependent upon the precision with which the scanning system is positioned, oriented, and moved if moved during the course of scanning. Utilizing coarse-adjustment levelling means, the temperature-scanning instrument (hereinafter referred to as the camera) can be brought up to the desired vertical height. It has been found advantageous that the central viewing direction of the camera be aimed right at a centerline of the wall surface to be scanned. It is particularly advantageous for the coarse-adjustment levelling means to be capable of adjusting motion within three mutually perpendicular planes of movement. The subframe in question additionally serves to accommodate control and recording equipment, and other such equipment used in performance of the method. In this way, the subframe can sturdily bear the weight of such cooperating equipment, with the mounting means for the camera itself, such as its carriage, being of very light and high-precision construction, which is particularly important if the scanning performed by the camera is in part implemented by shifting and/or swinging the camera in accordance with a preestablished velocity program.

The control and recording equipment just mentioned advantageously includes a television-type monitor to assist in the control and monitoring of the operation of the camera, and a recorder for recording the output data from the camera. The recorder can of course be a magnetic-tape recorder or indeed an electronic data storage operative for recording the camera output signals and other control information needed to interpret, reorganize and/or correct the camera output data. For back-up monitoring, if not provided by other means, use can be made of an oscilloscope connected to the output of the data storage, so that obvious malfunction of the system can be ascertained, and the cause of it removed, before for example going on to the next coke oven in the battery. The subframe can furthermore accommodate the control means for the preprogrammed shifting and/or swinging of the camera and/or for the preprogrammed control of its horizontal and/or vertical sweep or viewing angle and/or for the control of the coarse- and fine-adjustment levelling means for the arrangement, as well as other electrical components such as a power supply and the like.

The features just listed very greatly contribute to the accuracy, precision, quickness and convenience of the scanning operation to be performed and the set-up work preliminary thereto, and can be employed alternatively or cumulatively. When the one of the sweeps which is to be implemented is performed by e.g., shifting or swinging the camera, it is preferred that the camera be driven by a step motor, for high-precision control of its velocity at each point of its shifting or swinging motion, to assure that both at the wall-surface zones near to and far from the camera the scanned strips neither overlap nor have gaps between them.

If the horizontal and/or vertical sweep of the scanning operation is varied during the course of scanning, to take into account during the scanning itself the non-perpendicular orientation of the camera, then the non-cartesian organization of the camera output information is already at that point eliminated in at least one of the two sweep directions and to that extent need not be eliminated afterward by the computer. However, preprogrammed variation of the sweep action of one or both internal sweeps of such a camera during the actual course of the scanning operation does require tampering with the internal construction and/or operation of such a camera, and in general attempts to achieve cartesian organization of data in this way are economically feasible only where a large number of such systems intended for substantially identical use are to be produced and employed for relatively simple geometry-transformation problems.

The coarse- and fine-adjustment levelling means of the system preferably comprise numerically controlled pneumatic or hydraulic adjusters, to minimize the labor of operating personnel, facilitate in particular the setting-up work which such personnel must perform, and to facilitate repeatability.

Because the heat-image camera scans the wall surface of interest in a stripwise sequence, the camera must be mounted for movement in two dimensions. Depending upon the type of heat-image camera employed, this can be implemented using purely electronic deflection, i.e., as in ordinary television cameras, or else by exclusively mechanical means, or employing a combination of both techniques. However, it is preferred to employ half-mechanical or exclusively mechanical techniques, because these have been found to make it easiest to match the scanning operation to the geometry of the scanning problem faced. In general, the camera or the components thereof to be moved should have the largest possible range of movement, so that the system can be readily adapted to situations presenting different geometries.

However, no matter which of the aforementioned convenient mounting and adjustment features are employed, it is extremely important that the camera be mounted for precise levelling in three mutually perpendicular planes relative to the transportable subframe, and in a practical sense it is a virtual necessity that the means for performing such adjustments of the camera position and orientation be numerically controlled for precision setting-up work and repeatability.

Finally, it is necessary that the heat-image output data from the camera also include information concerning the start and/or end of the surface of interest, as a reference for electronic storage and interpretation of the heat-image data. The preferred way of generating this information is to locate temperature-reference structures at positions in the path of view of the camera corresponding to the start and end of the scanned surface. These temperature-reference structures are then picked up by the camera as the camera is scanning the first and/or last scanned strips of the wall surface. The temperature-reference structures can be of an enormous variety of forms, it only being important that they have temperatures which are different from those which can be expected for the wall surface itself, so that the output data from the camera contain a clear reference to the start and end of the scanned wall.

Depending upon the type of camera employed, the distance from the camera to the wall surface of interest, the temperatures to be encountered, and so forth, it may be advantageous or necessary to provide a part or even the whole of the apparatus with heat-shielding structure.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 3:
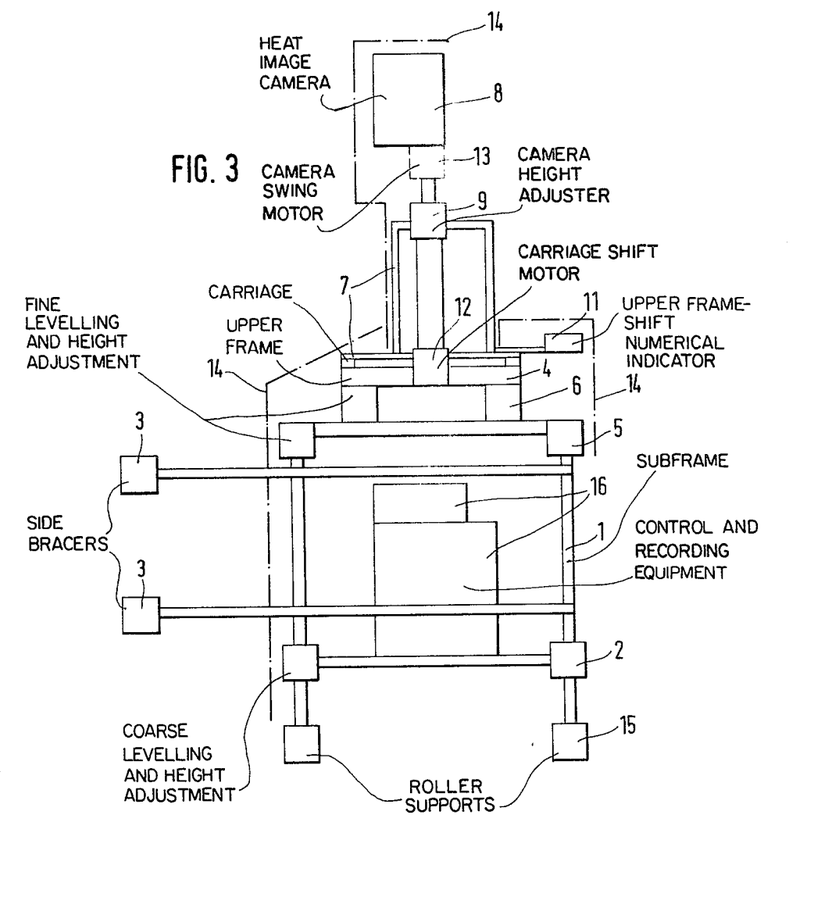
FIG. 3 is a schematic side view of the scanning system and its mounting structure, the system being positioned to peer leftward into the interior of a coking chamber, a row of such coking chambers extending in the direction perpendicular to the plane of the illustration.
Figure 4:
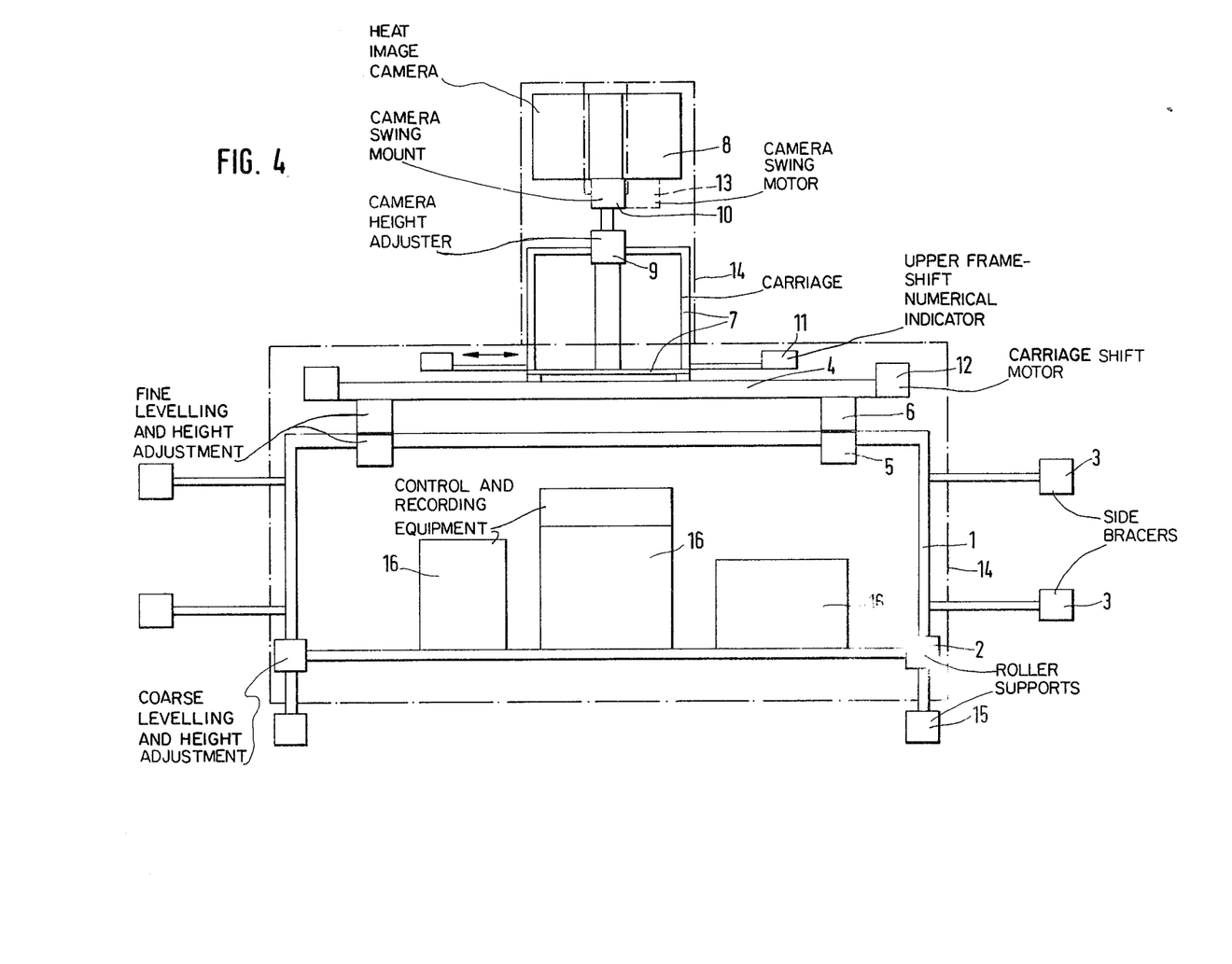
FIG. 4 is a front view of the system shown in FIG. 3.
Figure 5:
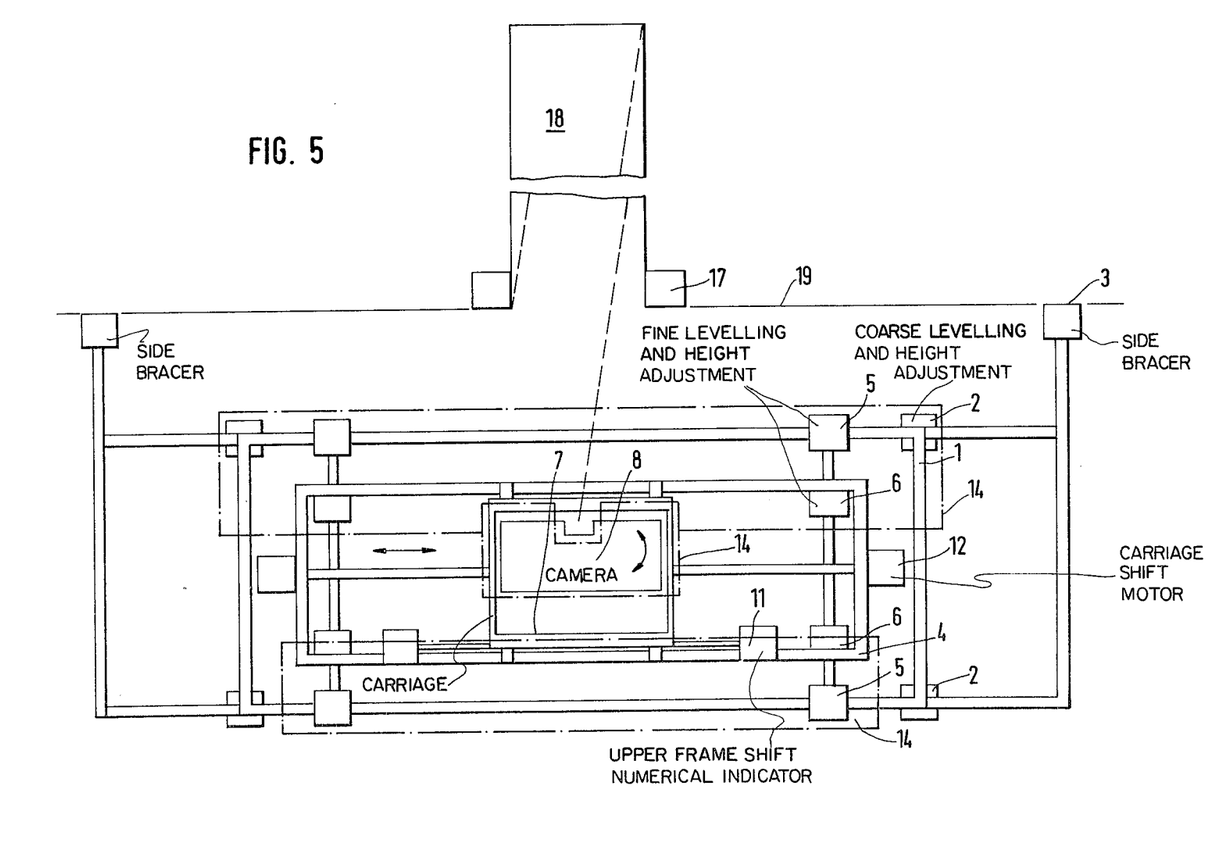
FIG. 5 is a top view of the system shown in FIGS. 3 and 4.

FIGS. 3, 4 and 5 are respectively side, front and top views of an exemplary embodiment of the invention. In FIG. 3, it is to be understood that a coking chamber (such as shown in FIG. 1a) is located to the left of the apparatus and extends leftwards a distance of 13 meters.

Numeral 1 denotes the subframe of the apparatus. Subframe 1 is provided at its bottom with means 15 transportably supporting the subframe 1 on the ground; supporting means 15 could e.g., be turnable or steerable wheels, or the like, i.e., so that subframe 1 can be moved from one coking chamber to the next in a battery of such chambers.

Numeral 2 denotes coarse-adjustment levelling and height-adjustment means provided at the four corners of the base of the subframe 1, for adjusting its height as a whole and for levelling it. Such coarse-adjustment levelling and height-adjusting means serves first to compensate for lack of levelness of the ground on which the apparatus rests, and second to raise the heat-image camera up to a height as closely as possible midway between the top and the base of the coking chamber into which it is to peer.

Numeral 3 denotes bracing and spacing means for fixing the apparatus in place by bracing it against the side of the coke-oven battery and properly spacing the apparatus from and parallel to the side of the coke-oven battery. For example, there may be four claws, an upper and lower one at the left and an upper and lower one at the right (see FIG. 4), each claw mounted on a screw spindle, the left and right claws engaging the usual left and right uprights bounding the end door of a coke oven, the screw spindles being turnable to properly space the apparatus from the side of the coke oven battery, preferably exactly parallel thereto.

The subframe 1 should be very rigid and stable and very rigidly and firmly supported on the ground. Numeral 4 denotes a highly rigid and inflexible upper frame, mounted on subframe 1 and precisely shiftable in three mutually perpendicular directions by fine-adjustment levelling and height-adjustment means 5 and 6. Measuring or indicating means 11 are provided for numerical control of the shifting movement of upper frame 4 in all three directions of shifting movement thereof. For example, measuring or indicating means 11 could be a numerical display which displays the x-, y- and z- coordinates of the shiftable upper frame 4, and possibly also its forward-backward and left-right tilts, to assist in setting-up work and in repeatability.

The measuring or indicating means 11 is mounted on a carriage 7. Carriage 7 is mounted on upper frame 4 for shifting movement in the direction perpendicular to the coking-chamber inrerior side wall of interest; i.e., carriage 7 is mounted for shifting movement perpendicular to the plane of illustration of FIG. 3. Carriage 7 and its mounting on upper frame 4 must be of very high quality, so that the carriage 7 can be shifted with utmost positioning precision and reliably keep whatever position it has been caused to assume at any given instant.

Carriage 7 mounts the heat-image camera 8. The mounting of camera 8 on carriage 7 includes the provision of fine-adjustment camera-height adjusting means 9 capable of changing the vertical height of the camera with a high degree of precision and resolution, and swing-mount means 10 (see FIG. 4) mounting the camera 8 on the carriage 7 for high-precision swinging movement relative to a vertical swing axis. Advantageously, the swing-mount means 10 could also include means for fine adjustment of the tilt of camera 8 relative to carriage 7.

The camera 8 itself is preferably enclosed within a heat-resistive housing having only a vertical slot-shaped opening at its front for the receipt of infrared radiation from the wall surface. In the illustrated embodiment, the wall surface of interest is a vertical wall (the interior left side wall of the coking chamber) and the camera scans this wall surface along successive vertical scan lines.

Numeral 12 denotes a high-precision drive mechanism, preferably a stepper-motor drive mechanism, operative for transversely shifting the carriage 7, i.e., in the direction perpendicular to the plane of illustration of FIG. 3. When drive 12 thusly shifts carriage 7, the camera 8 mounted on carriage 7, simply shifts as a whole transversely left-to-right past the open end door of the coking chamber of interest.

Numeral 13 denotes another such high-precision drive, again preferably a stepper-motor drive, operative for swinging the camera 8 as a whole about a vertical axis.

The two drives 12 and 13 are preferably stepper-motor drives because of the extremely high precision of positioning operation which stepper motors afford. The output shaft of a stepper motor, in response to an electrical command pulse applied to the electrical input of the motor's control circuitry, turns through a very precisely defined angle; this angle can be kept extremely small, by choosing a stepper motor having a small increment of turn and by providing the stepper motor with a speed-reducing output transmission. Thus, each time that an input pulse is applied to such a stepper motor, the motor output shaft turns through a small and well-defined incremental angle. By applying a train of such input pulses to the motor, the motor output shaft turns through a total angle equal to the incremental angle multiplied by the number of input pulses in such pulse train. By applying to the stepper motor a train of pulses whose inter-pulse spacing varies in accordance with a preprogrammed scheme, the angular position of the motor output shaft at any given instant during its turning motion, and also the angular speed of the output shaft at any given instant during its turning motion, can be controlled to implement any desired position-versus-time or velocity profile or program.

The preferred type of infrared heat-image camera (discussed in greater detail below) is conventional and is provided with internal means for deflecting the scanning spot of the camera in both the horizontal and vertical direction. In the preferred embodiment, one of these two internal sweep mechanisms is disabled, and that one of the two sweeps is instead implemented by shifting and/or swinging the camera as a whole. In the illustrated embodiment, the wall surface of interest is vertical, the internal horizontal-deflection control mechanism of the camera is disabled, the camera accordingly repeatedly performs a sweep along the length of a single vertical scan line, and the horizontal deflection is implemented from the outside by horizontally shifting and/or swinging the camera as a whole.

This horizontal motion of camera 8 as a whole can be implemented in two different ways in the illustrated embodiment:

1. Prior to the start of a left-to-right scan, the camera 8 is horizontally swung on swing-mount means 10 to a position in which it is properly aimed at the left interior side wall of the coking chamber. Then the left-to-right scan is performed by activating the high-precision stepper-motor drive mechanism 12 to shift the carriage 7 left-to-right (perpendicular to the plane of illustration of FIG. 3), so that the camera 8 is horizontally shifted left-to-right along the open end door of the coking chamber. When the left-to-right shift is finished, the camera 8 is horizontally swung on swing-mount means 10 to a position in which it is properly aimed at the right interior side wall of the coking chamber. Then a right-to-left scanning motion, for the scanning of the right side wall, is likewise performed by the drive mechanism 12, the latter causing the carriage 7 now to shift right-to-left. As already indicated, the use of a high-precision stepper-motor drive mechanism 12 makes it possible to preprogram the position-versus-time profile of this horizontal shifting motion (or equivalently the velocity profile of this horizontal shifting), so that, at each instant during the course of this horizontal shifting motion, where the camera will be located is preprogrammed and predetermined. In this way, the shift velocity of the camera carriage 7 can be preprogrammed to have a profile which takes into account the non-perpendicular aim of the camera to the wall surface. I.e., it will be clear that when scanning vertical strips of the near part of the wall surface a given amount of horizontal camera shift will cover a certain amount of wall surface (measured in the horizontal direction), whereas at the far part of the wall surface the same amount of horizontal camera shift will of course cover a greater amount of wall surface (measured in the horizontal direction). If the camera carriage 7 were shifted at constant velocity, it would follow that the number of vertical strips scanned at the near part of the wall surface would be considerably greater than the number of vertical strips scanned at the far part of the wall surface. By preprogramming the shift-velocity profile (the shifted-position versus time relationship) for the camera carriage 7, the spacing of scanned vertical strips of the wall surface can be made uniform proceeding left to right across the wall surface.

2. Instead of using the swing-mount means 10 to initially aim the camera and then the camera-shifting carriage 7 to perform the left-right sweep component, the roles can be reversed. Prior to the start of the left-to-right sweep of the left side wall, the carriage 7 is shifted rightward to a starting position, and the swing-mount means 10 used to aim the camera at the left side of the wall. The left-to-right sweep is then performed by the high-precision stepper-motor drive mechanism 13, the camera 8 swinging about a vertical axis left-to-right across the left side wall. Upon completion of the left-to-right sweep of the left side wall, the camera carriage 7 is shifted leftward and the swing-mount means 10 used to aim the camera for a sweep of the right side wall of the coking chamber, whereupon the horizontal sweep across the right side wall is then performed again by drive mechanism 13, which swings the camera to scan the right side wall.

As shown in FIGS. 3–5, heat-shielding cladding 14 clads the subframe 1, the camera carriage 7 and the camera 8, at least at the side of the apparatus which is to face the open coking chamber, inasmuch as temperatures near the open coking chamber may be on the order of 1200° C. Of course, the part of the cladding 14 which protects the front of the camera 8 must be provided with a vertical slot, so that the vertical-strip scan sweeps can occur.

As shown in FIGS. 3 and 4, the various control and recording equipment 16 needed for performance of the inventive method are mounted on the subframe 1, and preferably provided in a protective housing to protect this equipment from the dust and other environmental contaminants to which it otherwise could be exposed when located so close to an open coking chamber door.

In the illustrated embodiment, the upright frame members 17 (see FIG. 5) conventionally provided at the left and right sides of a coking-chamber end door are employed as temperature-reference structures. These upright frame members 17 will have a temperature distinguishably different from the temperature of the interior wall surfaces. As the camera sweeps along the left or right interior wall surface, when it encounters the transition between such wall surface and one of these upright frame members 17, the camera output data will include a corresponding clear indication, or reference, to which the start or end of a wall-scanning operation can be conveniently correlated.

Figure 6:
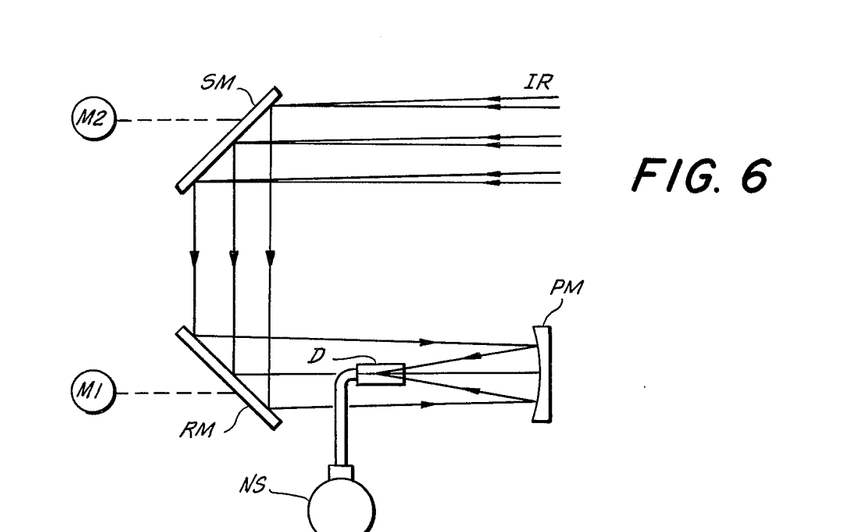
FIG. 6 is a simplified schematic illustration of one conventional type of infrared heat-image camera which can be used for the present invention.

For the camera itself, various conventional types of temperature-sensing scanning systems can be employed. It is presently preferred to employ a conventional infrared heat-image camera of the type whose horizontal and vertical deflection mechanisms mainly comprise motor-driven deflecting mirrors. FIG. 6 is a simplified schematic depiction of this type of conventional heat-image camera.

In FIG. 6 incoming infrared radiation IR is incident upon a swinging mirror SM, deflected by the latter onto a rotating mirror RM, deflected by the latter onto a parabolic mirror PM, and projected and focussed by the latter onto an infrared-radiation detector D. The detector D can, for example, be of the conventional indium-antimonide type and be nitrogen-cooled by nitrogen from a nitrogen source NS.

The swinging mirror SM is swingable or tiltable to a plurality of different positions, each position determining where an elongated scan line is to be. The rotating mirror RM rotates to implement the tracing of the elongated scan line established by swinging mirror SM; i.e., mirror SM establishes the scan line, and mirror RM then traces along the length of the selected scan line. In FIG. 6, the rotating mirror RM is shown driven by a motor M1, and the swinging mirror SM by a motor M2. These may be high-precision stepper motors, or motors of other types. The provision of separate motors M1, M2 to drive the rotating and swinging mirrors RM and SM, particularly when these are stepper motors, creates the possibility to correct for the perspective-caused non-cartesian organization of the heat-image data, by continual preprogrammed control of the velocities of these deflecting mirrors during the course of one surface-scanning operation; this possibility is discussed further below.

Typically, however, the rotating and swinging mirrors RM, SM are driven by a single drive motor, through respective transmissions, for the sake of simplicity and to minimize synchronization problems; instead, in the preferred embodiment of the present invention, this more typical conventional mirror-drive scheme is employed. The scan lines established by swinging mirror SM can of course be either vertical or horizontal, depending merely upon whether the infrared camera is mounted in normal upright orientation or laid on its side. In the illustrated application, the top and bottom of the wall to be scanned are located at equal distances from the camera, whereas the left and right sides of the wall are respectively located close to and far from the camera; accordingly, the scanning lines should be vertical scanning lines. If both of the camera's internal deflecting mechanisms were employed, the swinging mirror SM would establish where the vertical scanning line should be, whereas the rotating mirror RM would be responsible for scanning along the length of the selected scanning line. However, as already explained, in the preferred embodiment the horizontal-direction deflection is not performed by the internal deflecting mechanism of the camera, but instead by shifting and/or swinging the camera as a whole in the horizontal direction. Accordingly, the scan-line-selecting swinging mirror SM is kept permanently arrested in a predetermined angular position; cameras of this type conventionally have such a capability, for cases where line scanning instead of surface scanning is required. However, vertical deflection continues to be implemented by the rotating mirror RM, in the preferred embodiment.

Figure 7:
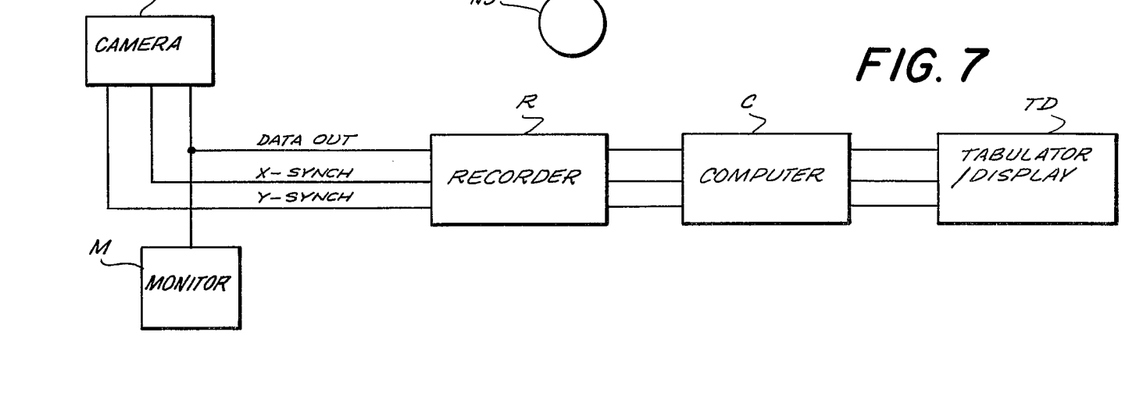
FIG. 7 depicts an embodiment of the inventive method, in which the output data from the scanning camera has a distorted organization, which is then transformed by computer into a cartesian organization.
Figure 8:
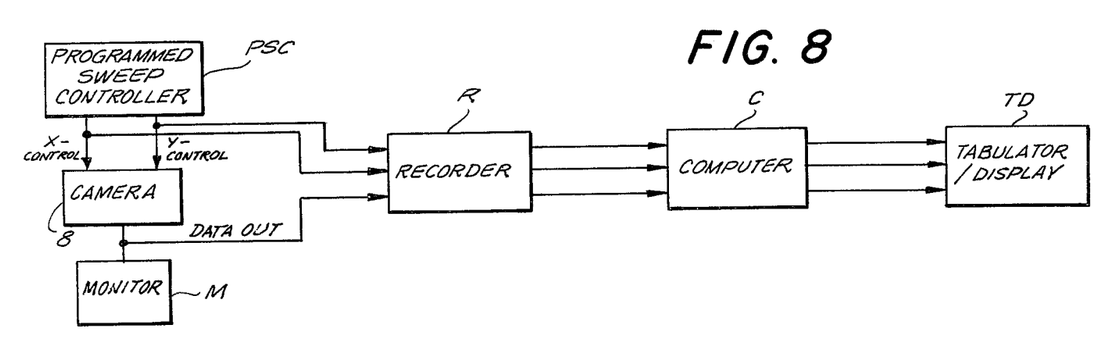
FIG. 8 depicts an embodiment of the inventive method, in which the horizontal and vertical sweep of the scanning camera are continually varied during scanning, so that the output data from the camera have a cartesian organization.
Figure 9:
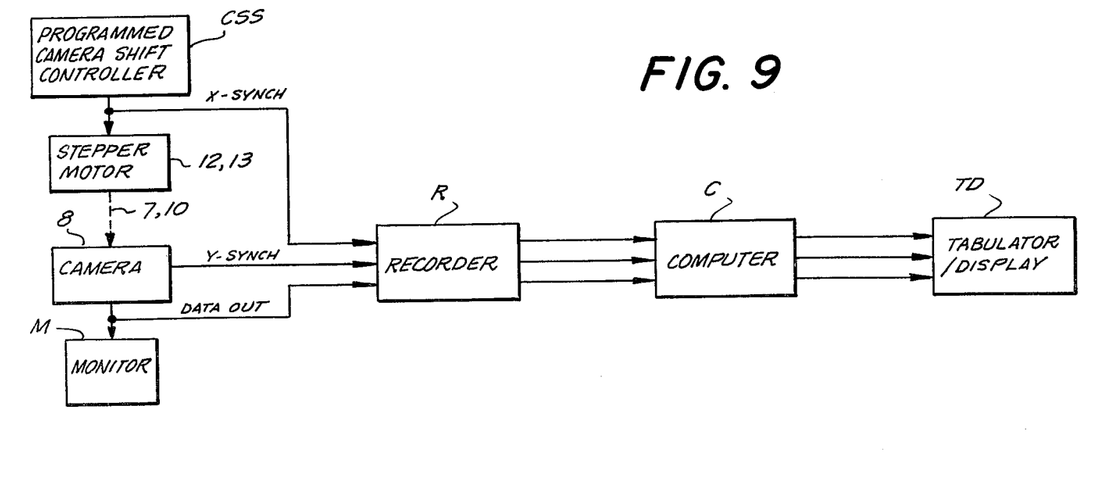
FIG. 9 depicts an embodiment of the inventive method, in which the horizontal sweep of the scanning camera is implemented by shifting or swinging the camera horizontally such that the transformation to cartesian organization of temperature data is performed in one direction prior to recording of the data, with the remainder of the transformation thereafter performed by computer.

FIGS. 7, 8 and 9 depict three versions of the invention technique, whose differences will make clearer the scope of the invention. In FIG. 7 the output data from the heat-image camera is of distorted, non-cartesian organization in both directions and must be reorganized and corrected. In FIG. 8, the output data from the camera is of cartesian organization. In FIG. 9, the preferred embodiment, the output data from the camera is of distorted, non-cartesian organization in only one of its two directions of organization.

In FIG. 7 a camera 8 of the conventional type schematically depicted in FIG. 6 is employed. The x-direction and y-direction internal deflection mechanisms of the camera are both utilized, in conventional manner, without any special modification. The camera is not shifted and/or swung horizontally for horizontal deflection, but instead is stationary during the surface-scanning operation. The image picked up by camera 8 substantially corresponds to what is shown in FIG. 1b, this image encompassing an image of the left interior wall of the coking chamber. The image of the left interior wall, considered in isolation, is trapezoidal as shown in FIG. 1b, in accordance with the distortion resulting from the elementary laws of optical perspective.

Clearly, considering the camera output data pertaining to this trapezoidal part of the image, the data is of correspondingly distorted, non-cartesian organization. Considering only the output data pertaining to the trapezoidal area of interest, first there are more vertical scan lines per horizontal unit distance at the left (nearer) part of the image than at the right (farther) part of the image. Accordingly, the x-direction density in the information of interest varies in the y-direction of information organization. Furthermore, still considering only the camera output data pertaining to the trapezoidal area of interest, the relevant part of each vertical scan line is a smaller and smaller fraction of the whole vertical scan line, proceeding left to right. I.e., the output data actually of interest is increasingly compressed or of increasing density as one proceeds left-to-right in the x-direction. Finally, the instantaneous size of the scanning spot may vary as a function of the x- and y-coordinates of the scanning spot, or equivalently as a function of the x- and y-values of scanning deflection. Clearly, to correct and transform the camera output data of actual interest, it is necessary first to isolate the data pertaining to the wall surface of interest, transform the perspective-distorted organization of this data into a cartesian organization, and apply to the data corrective factors which take into account the x/y-coordinate dependence of the scanning-spot surface area. (In some applications, the latter correction may not actually be of great importance, e.g., when the distance from the camera to the nearest part of the surface of interest does not so greatly differ from the distance to the farthest part of the surface of interest. It is to be noted that the instantaneous angular spread of the scanning beam in such infrared cameras is typically very acute, e.g., on the order of 0.05°.)

The camera output data is applied to a monitor M, for display of the ongoing scanning operation. This assists in the quick recognition of system malfunction or other situations which could detract from accurate operation. Typically, infrared cameras of this type come with an oscilloscope-type display screen for display of a two-dimensional heat-image.

The camera output data is furthermore applied to a recorder R which records this data. The recorder R could, for example, be a simple magnetic-tape data recorder, or of other conventional type, or could be an electronic data storage. The recorder R forms part of the equipment 16 mounted on the subframe 1. The camera 8 also transmits to the recorder R x-direction and y-direction deflection information, indicating at each successive instant during the scanning of vertical scanning lines the x-direction deflection value and the y-direction deflection value of the scanning beam. In this way, each instantaneous value of the recorded image data is accompanied by data indicating what the x- and y-deflection values of the scanning beam were. If the camera 8 is not provided with means for generating this x- and y-deflection value information, such means can readily be added and synchronized to the x-direction and y-direction scanning synch lines of the camera.

The information registered by recorder R is then read out and fed to a computer C. A very small-scale computer can be used, because the operations it is to perform are rather elementary and limited. The computer C receives the data for each vertical scan line traced during the surface-scanning operation. The computer is to isolate the data pertaining to the trapezoidal area of interest, transform the organization of this data from its perspective-distortion-based organization to cartesian organization, and also if necessary correct the data for scanning-spot surface-area variation. These tasks, considered individually, involve only elementary operations. Furthermore, these can be implemented in a variety of ways, which will be self-evident to persons skilled in the data-processing art. Conveniently, the computer C is programmed to operate on a vertical-scan-line basis, i.e., to separately handle data depending upon which scan line (#1, #2, #3, etc., left-to-right) the data belongs to.

To make a y-direction transformation to cartesian organization is particularly elementary. The computer C ascertains the number of the vertical scan line it is presently processing, e.g., scan line #125. The transformation program includes control data, indicating the start and end, within the data for scan line #125, of the part of that scan-line data actually encompassed by the trapezoidal area of interest. The geometry of the explanatory application illustrated is of course so simple that such control data can be easily predetermined. Thus, in effect, the computer C blanks out that portion of the scan-line-#125 data not corresponding to the trapezoidal area of interest. With respect to the scan-line-#125 data of actual interest, the computer samples and stored the n values of this data corresponding to n equidistantly spaced points of the relevant part of the scan line in question. Of course, n can be very large. For each such scan line, the computer blanks out the irrelevant parts of the scanline data, and then samples the values of the relevant data corresponding to n equidistantly spaced points. It will be evident that the thusly sampled data, n values per scan line, are the equivalent of a y-direction stretching of the trapezoidal organization of data into a cartesian organization of information.

The x-direction transformation into cartesian organization is equally simple. If the infrared camera were aimed perpendicularly at the wall, and at a sufficient distance from the wall, the horizontal spacing between neighboring vertical scanned strips would be equal, all across the wall proceeding left-to-right, whereas with the trapezoidal perspective-based distortion of information organization, the inter-scan-line spacing increases going left-to-right. To effect the y-direction transformation into cartesian organization, it is merely necessary to equalize the spacing. Because the geometry of the situation is predetermined, the x-deflection value registered along with the data for each vertical scan line indicates, for the given geometry, which vertical strip on the wall is involved, and the computer merely assigns to the data pertaining to one scan line the corresponding cartesian x-coordinate value.

Accordingly, the computer has generated for the relevant part of the data for each single scan line, a cartesian x-coordinate value for that scan line, and n equidistantly sampled values, thereby achieving the desired transformation into simple cartesian organization. Of course, in itself, i.e., considered abstractly, this is an elementary problem which rather simple computers can perform in a great variety of different ways. What makes the problem elementary is the fact that the geometry is completely predetermined, and does not rise above the level of trigonometry.

Finally, if the application involved makes it necessary, the computer can also correct the data (before or after the transformation into cartesian organization), to take into account the x/y-dependence of the scanning-spot surface area. If the wall is so large and so oriented that the parts of its nearest to and farthest from the camera are of greatly differing distances from the camera, e.g., in the case of a long wall, the surface area instantaneously covered by the scanning spot at wall portions farthest from the camera will evidently be larger than the surface area instantaneously covered by the scanning spot at wall portions nearest to the camera, because the instantaneous angular spread of the scanning beam, although it may be as small as 0.05°, is nevertheless not zero. However, here again, all camera output data recorded by recorder R is accompanied by x-deflection and y-deflection values, and because the geometry of the situation is completely predetermined, so also is the true scanning-spot size for every given instant during the wall-scanning operation. Acordingly, the computer C can readily correct the camera output data, before or after transformation into cartesian organization, so as to correct or equalise for x/y-dependence of scanning-spot surface area.

The camera output data now having been transformed into cartesian organization and also corrected for the x/y-dependence of scanning-spot surface area, the resultant data can be read out from the computer directly and applied to a conventional tabulator/display unit TD, to produce an output display such as shown in FIG. 2. Of course, unit TD could be a CRT display unit, a printer, or the like. The output information can consist of a tabulation of numerical temperature values having a rectangular organization, and/or could for example consist of temperature-range zone displayed by means of different color, different light intensity, different symbols (e.g., X's for temperatures in one range, *'s for temperatures in a second range, and so forth), and other such possibilites conventional in the data-display art.

In the technique of FIG. 7, the camera output data received by recorder R is completely non-cartesian in its organization. FIG. 8 depicts an alternative, not presently preferred, in which the situation is the opposite; the data received by recorder R is already in cartesian organization. This is achieved by continually varying the x-deflection and y -deflection sweep speeds of the scanning camera, during the ongoing course of the wall-scanning operation, to take into account already at that stage the trapezoidal perspective-based distortion in the geometry of the situation. To this end, the x-deflection mirror and the y-deflection mirror internal to the camera must be provided with separate drive mechanisms, e.g., the high-precision stepper-motor drive mechanisms shown in FIG. 5. Of course, here again, the geometry of the situation is completely predetermined, and it is an elementary matter to establish the requisite x-direction sweep-speed program and the requisite y-direction sweep-speed program. After these sweep-speed programs have been established, they are stored in a programmed sweep controller PSC, which applies corresponding trains of command pulses to the x- and y-direction drives of the camera's internal sweep mechanisms. Reference to FIG. 1b will make clear that, to transform into cartesian organization by continual adjustment of x- and y-sweep speed, requires that both the x- and y-sweep speeds be progressively decreased as the scanning proceeds in the x-direction left-to-right. The x- and y-sweep-speed decrease programs follow directly from the geometry of the situation.

Accordingly, in FIG. 8, the camera output data applied to recorder R is already in cartesian organization, and the computer C need only apply to this data corrective factors compensating for the x/y-dependence of the instantaneous value of the scanning-spot surface area, in applications where that might be a problem. To be able to do that, the computer C can receive, as in FIG. 7, instantaneous x- and y-coordinate values accompanying the instantaneous camera output data, so as to be informed of where the scanning spot was for each datum processed.

The technique depicted in FIG. 8 is not preferred at the present time, because external control of the internal sweep mechanisms can be somewhat costly to implement, particularly where the camera's internal sweep mechanisms are mechanical in operation, not electronic. It is presently preferred to use the simplest possible deflection-mirror-type infrared camera, having a single drive motor driving both deflection mirrors, to minimize cost in general and to avoid complicated internal sweep synchronization difficulties.

FIG. 9 depicts the preferred approach. Here, the camera output data is semi-cartesian, i.e., cartesian with respect to the x-direction but distorted (compressed and expanded relative to cartesian organization) in the y-direction. This is a hybrid of the two extreme techniques depicted in FIGS. 7 and 8, and utilizes the best features in these two techniques. In particular, the y-direction transformation into cartesian coordinates (i.e., the vertical "stretching" of data) performed by computer C in FIG. 7 is extremely easy to implement on a simple computer, and therefore advantageous. More importantly, the computer-performed y-direction transformation can create no resolution problems. In contrast, the computer-performed x-direction transformation in FIG. 7, although likewise easy to implement on a simple computer, can produce resolution limitations. As already explained, with the trapezoidal distortion of information being discussed, there is a greater density of vertical scan lines at the nearer part of the wall surface than at the farther part of the wall surface, this density decreasing going left-to-right in FIG. 1b.

Although this progressive decrease in scan-line density in the left-to-right direction can readily be equalized by the computer C in a very elementary way, the fact remains that, physically, there is x-direction variation in the density or distribution of the scanned physical strip-shaped zones of the physical wall surface itself; i.e., the left (nearer) half of the wall will be subjected to a greater number of line-scan operations than the right (farther) half of the wall, when one uses the FIG. 7 technique, and the computer C, although it can directly correct for this in so far as data organization is concerned, cannot change the basic fact. Of course, no such problem arises with the technique of FIG. 8, but there it is necessary to preprogram the operation of the camer's internal deflection mechanism, which can be costly.

The preferred hybrid technique of FIG. 9 takes in the best of both FIGS. 7 and 8. The y-direction aspect of the transformation into cartesian organization is computer-performed as in FIG. 7. In contrast, the x-direction aspect of the transformation is performed, as in FIG. 8, by preprogrammed progressive adjustment of the x-direction deflection speed, i.e., so that the camera output data received by recorder R already is in cartesian organization with respect to the x-direction. However, to avoid the need to interfere with the camera's internal x-direction sweep mechanism, the x-direction deflection is performed not internally of the camera, but instead by horizontally shifting and/or swinging the camera as a whole, i.e., as explained earlier with respect to FIGS. 3-5. This permits the use of simple and reliable commercially available infrared cameras, without any modification of their internal operation. The scan-line-selecting deflector mechanism of the camera (e.g., the swinging mirror SM in FIG. 6) is arrested in a fixed position and does not perform sweeps; conventional infrared cameras are often designed to be selectably operated in this way. The sweep not performed by the disabled one of the two internal sweep mechanisms is performed by shifting and/or swinging the camera 8 as a whole.

FIG. 9 schematically depicts what has already been explained with reference to the preferred embodiment of FIGS. 3-5. A programmed camera-shift controller CSC applies command pulse trains to one or both of the stepper-motor drive mechanisms 12, 13, thus horizontally shifting carriage 7 and camera 8 and/or swinging camera 8, in accordance with the preprogrammed velocity versus time schedule. This schedule is selected such that the number of vertical scan lines traced upon the wall surface per unit horizontal distance is constant across the wall surface. I.e., the number of vertical scan lines thrown onto the actual left half of the wall surface will be equal to the number of vertical scan lines thrown onto the actual right half of the wall surface. Accordingly, the x-direction organization of camera output data is already cartesian, and the computer C is not called upon to change x-direction data organization as a preliminary to print-out or display. The y-direction aspect of transformation into cartesian organization is performed in the same way as in FIG. 7. As before, if the application involved makes it appropriate to correct for x/y-dependence of scanning-spot size the computer C applies to each camera output datum (before or after the completion of the transformation into cartesian organization) the corrective factors dictated by the x- and y-coordinates of that datum in conjunction with the predetermined geometry involved. For this purpose, as in FIGS. 7 and 8, the recorder R receives, along with camera output data, x- and y-deflection values, the y-deflection values in the same way as in FIG. 7, the x-deflection values from the x-deflection-governing camera shift controller CSC.

After the system has been set up for the geometry of a particular problem, the repeatability of the setting-up work facilitated by the numerically controlled height, position and orientation adjusters in the structure of FIGS. 3–5, thereafter permits very quick generation of the desired two-dimensional temperature profile data, whenever needed. Thus, the system depicted in FIGS. 3–5 can be moved from one coking chamber to the next in a battery of such chambers, and ascertain the surface-temperature profiles of the internal walls of interest, as often as that information may be of interest.

While the illustrated system has its greatest significance when viewing a large surface at an angle so extreme that the direction of view is almost parallel to the surface of interest, as in the case of a very narrow and very deep coking chamber, it is of course equally applicable where the direction of view is not so drastically non-perpendicular, and is applicable for directions of view anywhere from close to 0° up to an unproblematic 90°.

It will be understood that each of the elements described above, or two or more together, may also find a useful application in other types of constructions and procedures differing from the types described above.

While the invention has been illustrated and described as embodied in the scanning of coking-chamber interiors it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method of ascertaining the surface temperature distribution over the whole of a surface of interest when the surface of interest is so located as to prevent a temperature-sensitive scanning system from being aimed at such surface perpendicular thereto, the method comprising scanning the surface of interest using a temperature-sensitive scanning system which is operative for scanning in a first direction along the lengths of successive scan lines, the successive scan lines succeeding each other in a second direction transverse to the first direction, with the temperature-sensitive scanning system during this scanning being aimed at the surface of interest at an arbitrary angle of less than 90° relative thereto, whereby the temperature image of the surface of interest as presented to the temperature-sensitive scanning system is distorted in accordance with the laws of optical perspective; and processing the output data from the temperature-sensitive scanning system in accordance with said arbitrary angle to form a record of the temperature image transformed into cartesian form simulating the temperature image which would have been presented to the temperature-sensitive scanning system had the temperature-sensitive scanning system been aimed perpendicular to the surface of interest.

2. The method as set forth in claim 1, further comprising controlling the operation of the temperature-sensitive scanning system to cause the system to follow a scanning schedule which is cartesian in both the direction of elongation of the scan lines and in the direction in which successive scan lines succeed one another, whereby the content and organization of the output data from the temperature-sensitive scanning system directly correspond to the distorted non-cartesian temperature image presented to the temperature-sensitive scanning system, the processing of the output data of the scanning system including using a computer to transform the organization of the scanning-system output data into an organization corresponding to the temperature image which would have been presented to the scanning system had the scanning system been aimed perpendicular to the surface of interest.

3. The method of claim 1, further comprising controlling the operation of the temperature-sensitive scanning system to cause the output data produced by the scanning system to have an organization which is cartesian in both said first and second directions and which corresponds to the temperature image which would have been presented to the scanning system had it been possible to aim the temperature-sensitive scanning system perpendicular to the surface of interest, this comprising causing the temperature-sensitive scanning system to follow a scanning schedule which is non-cartesian in both said first and second directions and which geometrically compensates for the distorted non-cartesian temperature image actually presented to the scanning system.

4. The method of claim 1 further comprising, controlling the operation of the temperature-sensitive scanning system to cause the output data produced by the scanning system to have an organization which is cartesian with respect to one of said two directions and which corresponds, but only with respect to said one direction, to the temperature image which would have been presented to the scanning system had the scanning system been aimed perpendicular to the surface of interest, this comprising causing the temperature-sensitive scanning system to follow a scanning schedule which is non-cartesian in said one direction and which geometrically compensates, but only with respect to said one direction, for the distorted non-cartesian temperature image actually presented to the scanning system, the organization of the output data produced by the scanning system, with respect to the other of said two directions, being non-cartesian and corresponding to the distorted non-cartesian temperature image actually presented to the scanning system, said processing of the output data of the scanning system including using a computer to transform the organization of the scanning-system output data, with respect said other direction, into an organization corresponding to the temperature image which would have been presented to the scanning system had the scanning system been aimed perpendicular to the surface of interest.

5. The method of claim 4, wherein
said one of said two directions being said second direction.

6. The method of claim 4, therein
said one of said two directions being said second direction further comprising,
the step of causing the temperature-sensitive scanning system to follow a scanning schedule which is non-cartesian in said one direction comprises displacing the temperature-sensitive measuring system in said second direction during the course of the scanning of the surface of interest with a preprogrammed progressively changing velocity which geometrically compensates, with respect to said second direction, for the distorted non-cartesian temperature image presented to the scanning system.

7. The method of claim 1 further comprising, using for the temperature-sensitive scanning system a passive infrared scanning system.

8. An apparatus for scanning poor-access surfaces, the apparatus comprising a subframe; means supporting the subframe for movement to and from a location where the scanning of a surface of interest is to be performed; arresting means for arresting the subframe against further such movement when the subframe has been moved to the location where the scanning is to be performed; the means supporting the subframe including coarse-adjustment levelling means for adjusting the inclination of the subframe as a whole in a plurality of directions; a temperature-sensitive scanning system operative for scanning in a first direction along the length of a scan line; means mounting the scanning system on the subframe; recording means mounted on the subframe, connected to the scanning system and operative for recording output data produced by the scanning system; the means mounting the scanning system including fine-adjustment levelling and positioning means for finely adjusting the position and orientation of the scanning system relative to the subframe; means coupled to the fine-adjustment levelling and positioning means, operative for quantitatively indicating the position and orientation of the scanning system relative to the subframe; the means mounting the scanning system furthemore including means mounting the scanning system for controlled displacement in a second direction transverse to said first direction; a drive motor operative for displacing the scanning system in said second direction to thereby displace said scan line in said second direction; and motor-control means operative for causing said drive motor to displace the scanning system in said second direction with a preprogrammed velocity versus time.

9. The apparatus of claim 8; furthermore including a monitor mounted on the subframe, connected to the scanning system and operative during scanning for displaying the data being generated by the scanning system.

10. The apparatus of claim 8; furthermore including heat-shielding cladding covering at least that part of the apparatus which is to be faced towards a surface to be scanned.

11. The apparatus of claim 8; furthermore including means for engaging the apparatus to the side of a battery of coking chambers and adjusting the orientation of the apparatus relative to the side of such battery of coking chambers; heat-shielding cladding covering at least that part of the scanning system which is to face towards coking chambers; and heat-shielding cladding covering at least that part of the subframe which is to face towards the coking chambers, the cladding of the camera and that of the subframe being separate to facilitate movement of the scanning system relative to the subframe but being overlapping.

12. The apparatus of claim 8, the scanning system comprising an infrared camera, the camera being of the type including an infrared detector and a rotating deflecting mirror operative for tracing a scan line by deflecting onto the infrared detector radiation emanating from successive portions of a surface being scanned.

* * * * *